United States Patent [19]

Winter et al.

[11] 3,944,566
[45] Mar. 16, 1976

[54] TRICYCLIC SUBSTITUTED AMINOALCOHOLS

[75] Inventors: Werner Winter, Viernheim; Max Thiel, Mannheim; Kurt Stach, Mannheim-Waldhof; Egon Roesch, Mannheim An Oberen Luisenpark; Gisbert Sponer, Hemsbach, all of Germany

[73] Assignee: Boehringer Mannheim GmbH, Mannheim, Germany

[22] Filed: June 28, 1974

[21] Appl. No.: 484,353

[30] Foreign Application Priority Data
July 14, 1976   Germany............................. 2335943

[52] U.S. Cl. ................ 260/328; 260/333; 260/335; 260/570.8 TC; 424/275; 424/278; 424/283; 424/330
[51] Int. Cl.² ......................................... C07D 335/20
[58] Field of Search ........ 260/327 B, 328, 333, 335, 260/570.8 TC

[56] References Cited
UNITED STATES PATENTS

| | | | |
|---|---|---|---|
| 3,285,919 | 11/1966 | Faust et al. .......................... | 260/268 |
| 3,535,315 | 10/1970 | Winter et al. ....................... | 260/240 |
| 3,872,102 | 3/1975 | Malen et al. ....................... | 260/327 B |

FOREIGN PATENTS OR APPLICATIONS

| | | | |
|---|---|---|---|
| 1,552,851 | 12/1968 | France ................................ | 260/328 |

*Primary Examiner*—John D. Randolph
*Assistant Examiner*—C. M. S. Jaisle
*Attorney, Agent, or Firm*—Burgess, Dinklage & Sprung

[57] ABSTRACT

New tricyclic substituted aminoalcohols of the formula:

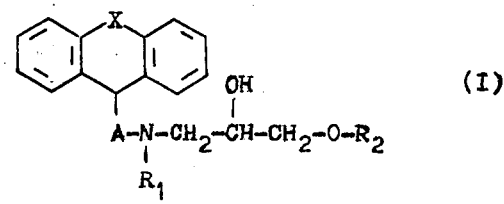

wherein
  X is ethylene, vinylene, oxygen, sulfur, or oxamethylene,
  A is straight-chained or branched alkylene of from 2 to 5 carbon atoms,
  $R_1$ is alkyl of up to 3 carbon atoms; and
  $R_2$ is cyclohexyl or phenyl;
and the physiologically compatible salts thereof; possess outstanding and valuable cardiac and circulatory activity.

13 Claims, No Drawings

TRICYCLIC SUBSTITUTED AMINOALCOHOLS

The present invention relates to new tricyclic substituted aminoalcohol compounds and to therapeutic compositions containing them.

German Pat. No. 1,568,145 describes certain tricyclic substituted aminoalcohols with valuable cardiac and circulatory activity; however, only those compounds are effectively disclosed in which the amino group still bears a free hydrogen atom.

We have now found that a special group of these tricyclic substituted aminoalcohols in which the nitrogen atom of the amino group bears, as third substituent, an alkyl radical, possesses especially advantageous properties, particularly with regard to the length of action.

Thus, according to the present invention, there are provided tricyclic substituted aminoalcohols of the formula:

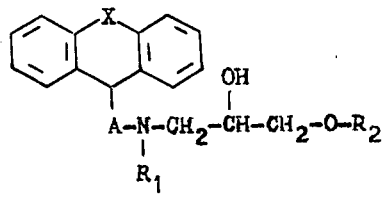

(I)

wherein
X is ethylene, vinylene, oxygen, sulfur, or oxamethylene,
A is straight-chained or branched alkylene of from 2 to 5 carbon atoms,
$R_1$ is alkyl of up to 3 carbon atoms; and
$R_2$ is cyclohexyl or phenyl;
and the physiologically compatible salts thereof.

The new compounds (I) of the present invention can be prepared by reacting a compound of the formula:

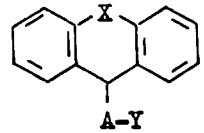

(II)

with a compound of the formula:

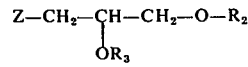

(III)

wherein A, X and $R_2$ have the same meanings as above and one of the symbols Y and Z represents a reactive group, whereas the other one is an —NH—$R_1$ group, wherein $R_1$ has the same meaning as above, and $R_3$ is hydrogen or, together with Z, represents an additional valency bond, whereafter, if desired, the compounds obtained are converted into their physiologically compatible salts.

The reaction of the compounds of formulae (II) and (III) can be accomplished simply by heating the reaction components. If desired, however, the reaction can be carried out in the presence of an inert, high boiling solvent.

If, instead of the epoxides of formula (III), there are used the corresponding halohydrins, then, for the binding of the hydrogen halide split off, it is preferable to add a base, for example, an excess of the amine of formula (II).

The reactive residue Y or Z, respectively, in formulae (II) and (III) can be, for example, halogen, mesyloxy or tosyloxy.

The basic reaction products can be reacted with inorganic and organic acids to give the corresponding physiologically compatible salts. As inorganic acids, there can be used, for example, hydrohalic acids, sulfuric acid and phosphoric acid and as organic acids, for example, acetic acid, lactic acid, maleic acid, fumaric acid, tartaric acid and citric acid.

The following Examples illustrate the invention:

EXAMPLE 1

Preparation of
N-Methyl-N-([2-(6,11-dihydrodibenz[b,e]oxepin-11-yl-ethyl]-1-amino-3-phenoxypropan-2-ol

Method A 27.15 g. (0.15 mol) 1-phenoxy-2-hydroxy-3-methylaminopropane were heated under reflux for 6 hours with 47.7 g. (0.15 mol) 11-mesyloxyethyl-6,11-dihydrodibenz[b,e]oxepine in 150 ml. dioxan in the presence of 21.9 g. (0.17 mol) ethyl diisopropylamine. The reaction mixture was subsequently evaporated in a vacuum and the residue was taken up in ether, with the addition of some ethyl acetate, shaken out twice with water and the organic phase separated off and evaporated in a vacuum. The residue consisted of 44.6 g. (74% of theory) of the chromatographically almost pure end product, which was taken up in 50 ml. alcohol. This was mixed with an alcoholic solution of fumaric acid and diluted with ether. The reaction mixture was left to stand overnight, whereafter the precipitate obtained was filtered off with suction. There were obtained 28.9 g. (40.9% of theory) of the fumarate of N-methyl-N-[2-(6,11-dihydrodibenz[b,e]oxepin-11-yl)-ethyl]-1-amino-3-phenoxy-propan-2-ol, which had a melting point of 131° – 132°C. After recrystallization from isopropanol, with the addition of some ether, the melting point remained unchanged.

The starting materials were prepared in the following manner:

6,11-Dihydrodibenz[b,e]oxepin-11-yl-acetic acid 30 g. (0.128 mol) 6,11-dihydrodibenz[b,e]oxepin-11-yl-acetonitrile were heated under reflux for 8 hours in 300 ml. alcohol with 40 g. sodium hydroxide and 40 ml. water. Subsequently, the reaction mixture was substantially evaporated in a vacuum and the residue was taken up in water and then extracted with ether. The aqueous phase was then acidified and the precipitate was filtered off with suction. After drying, there were obtained 30 g. (92.5% of theory) of the desired 6,11-dihydrodibenz[b,e]-oxepin-11-yl-acetic acid, which had a melting point of 114° – 115°C.

Ethyl 6,11-dihydrodibenz[b,e]oxepin-11-yl-acetate 29 g. (0.114 mol) 6,11-dihydrodibenz[b,e]oxepin-11-yl-acetic acid were heated under reflux for 4 hours in 200 ml. ethanolic hydrochloric acid. The reaction mixture was subsequently evaporated to give 31.1 g. (96.6% of theory) of the desired ester in crude form. After high vacuum distillation, there were obtained 27.4 g. (85.1% of theory) ethyl 6,11-dihydrodibenz[b,e]oxepin-11-yl-acetate, which had a boiling point of 170° – 173°C./0.1 mm.Hg.

6,11-Dihydrodibenz[b,e]oxepin-11-yl-ethanol 27 g. (0.096 mol) ethyl 6,11-dihydrodibenz[b,e]oxepin-11-yl-acetate were added dropwise, with cooling, to a suspension of 3.8 g. (0.1 mol) lithium aluminum hydride in 300 ml. ether. The reaction mixture was subsequently stirred for 2 hours at ambient temperature, decomposed by the addition of a saturated aqueous solution of sodium chloride and the precipitated hydroxides were filtered off with suction and the filtrate was evaporated. The residue consisted of practically pure 6,11-dihydrodibenz[b,e]oxepin-11-yl-ethanol in a yield of 22.4 g. (97.5% of theory). 10 g. of this product were distilled in a high vacuum. There were obtained 9.0 g. of the product with a boiling point of 158° – 159°C./0.2 mm.Hg.

11-Mesyloxyethyl-6,11-dihydrodibenz[b,e]oxepine 22 g. (0.092 mol) 6,11dihydrodibenz[b,e]oxepin-11-yl-ethanol were mixed in 75 ml. pyridine at 0°C. with 23.5 ml. (0.3 mol) methane-sulfochloride. The reaction mixture was subsequently stirred for 30 minutes at 0°C. and for 60 minutes at ambient temperature and the reaction mixture was then poured on to ice. The mixture obtained was subsequently extracted with ether, the ethereal layer was shaken out with dilute hydrochloric acid and with water and the organic layer was dried and evaporated. The desired mesylate was obtained in yield of the crude product of 28.1 g. (96.6% of theory). A sample thereof was triturated with ligroin to give 11-mesyloxyethyl-6,11-dihydrodibenz[b,e]oxepine with a melting point of 64° – 66°C.

1-Phenoxy-2-hydroxy-3-methylaminopropane 50 g. (0.333 mol) phenyl glycidyl ether were heated in 250 ml. tetrahydrofuran, saturated with methylamine, for 4 hours at 100°C. in an autoclave. The tetrahydrofuran was subsequently distilled off. There was obtained a residue of about 60 g. (practically 100% yield) 1-phenoxy-2-hydroxy-3-methylaminopropane. High vacuum distillation of this product gave 47.4 g. (78.57% of theory) 1-phenoxy-2-hydroxy-3-methylaminopropane, which had a boiling point of 120° – 125°C./0.2 mm.Hg.

Method B 4 g. (0.0158 mol) 11-methylaminoethyl-6,11-dihydrodibenz[b,e]oxepine and 2.6 g.(0.0173 mol) phenyl glycidyl ether were heated for 4 hours at 120°C. The reaction mixture was then cooled and dissolved in alcohol and the alcoholic solution thus obtained was mixed with an alcoholic solution of fumaric acid. After the addition of some ether, 5.0 g. (68.6% of theory) of the fumarate of N-methyl-N-[2-(6,11-dihydrodibenz[b,e]oxepin-11-yl)ethyl]-1-amino-3-phenoxypropan-2-ol crystallized out; it had a melting point of 131° – 132°C. The melting point remained unchanged after recrystallizing once from isopropanol/ether.

The starting materials were prepared in the following manner:

11-Formylaminoethyl-6,11-dihydrodibenz[b,e]oxepine 23.9 g. (0.1 mol) 11-aminoethyl-6,11-dihydrodibenz[b,e]oxepine were heated under reflux for 5 hours with 80 ml. ethyl formate, with the addition of 2 ml. water. Subsequently, the reaction mixture was evaporated in a vacuum, the residue was taken up in ether and the ethereal solution was shaken out with dilute hydrochloric acid and subsequently with water. The organic phase was evaporated, after drying. There was obtained a residue of 25.4 g. (95.1% of theory) 11-formylaminoethyl-6,11-dihydrodibenz[b,e]oxepine, which was chromatographically pure and can be further worked up in this form.

11-Methylaminoethyl--6,11-dihydrodibenz[b,e]oxedine.

25.0 g. (0.094 mol) 11-formylaminoethyl-6,11-dihydrodibenz[b,e]oxepine were reduced with 7.1 g. (0.187 mol) lithium aluminum hydride in 500 ml. anhydrous ether and 30 ml. tetrahydrofuran by stirring for 2.5 hours at ambient temperature. The reaction mixture was left to stand overnight, then decomposed with a saturated aqueous solution of sodium chloride and the inorganic material filtered off with suction. The organic layer was shaken out with 1N hydrochloric acid and the aqueous acidic layer subsequently rendered alkaline. The separated oil was isolated by extraction with ether. After evaporating the dried ethereal extract, there were obtained 21.1 g. (89.0% of theory) crude 11-methylaminoethyl-6,11-dihydrodibenz[b,e]oxepine. After high vacuum distillation, there were obtained 18.2 g. (77% of theory) of pure product, which had a boiling point of 154°–16°C./0.1 mm.Hg.

The following compounds were obtained in an analogous manner, according to Method A or B:

N-Methyl-N-[2-xanthen9-yl)-ethyl]-1-phenoxy-3-aminopropan-2-ol by the reaction of N-methyl-N-2-(xanthen-9-yl)-ethylamine (hydrochloride: m.p. 241° – 242°C., obtained from N-formyl-N-2-(xanthen-9-yl)-ethylamine; m.p. 120° – 121°C.) with phenyl glycidyl ether; yield 48% of theory; m.p. of the hydrochloride: 241° – 242°C.;

N-methyl-N-[2-(thiaxanthen-9-yl)-ethyl]-1-phenoxy-3-aminopropan-2-ol by the reaction of N-methyl-N-2-(thiaxanthen-9-yl)-ethylamine (b.p. 150° – 153°C./0.05 mm.Hg.; from N-formyl-N-2-(thiaxanthen9-yl)-ethylamine; m.p. 92° – 94°C.) with phenyl glycidyl ether; yield 76.7% of theory; m.p. of the oxalate 121°C.

N-methyl-N-[2-(10,11-dihydro-5H-dibenzo[a,d]cyclohepten-5-yl)ethyl]-1-phenoxy-3-aminopropan-2-ol by the reaction of 1-mesyloxy-2-(10,11-dihydro-5H-dibenzo[a,d]cyclohepten-5-yl)-ethane (b.p. 77° – 80°C.) with 1-phenoxy-2-hydroxy-3-methylaminopropane; yield 52% of theory; m.p. of the oxalate: 130° – 132°C.;

N-ethyl-N-[1,1-dimethyl-2-(10,11-dihydro-5H-dibenzo[a,d]cyclohepten-5-yl)-ethyl]-1-phenoxy-3-aminopropan-2-ol by the reaction of N-ethyl-N-1,1-dimethyl-2-(10,11-dihydro-5H-dibenzo[a,d]cyclohepten-5-yl)-ethylamine (b.p. 136° – 145°C./0.05 mm.Hg.; from N-acetyl-N-1,1-dimethyl-2-(10,11-dihydro-5H- dibenzo[a,d]cyclohepten-5-yl)-ethylamine; m.p. 139°–142°C.) with phenyl glycidyl ether; yield 76.2% of theory; m.p. of the hydrochloride: 165° – 167°C.;

N-methyl-N-[3-(10,11-dihydro-5H-dibenzo[a,d]cyclohepten-5-yl)propyl]-1-phenoxy-3-aminopropan-2-ol by the reaction of 1-mesyloxy-3-(10,11-dihydro-5H-dibenzo[a,d]cyclohepten-5-yl)-propane (m.p. 72° – 74°C.) with 1-phenoxy-2-hydroxy-3-methylaminopropane; yield 45.2% of theory; the compound was isolated as its amorphous citrate;

N-ethyl-N-[2-(6,11-dihydrodibenz[b,e]oxepin-11-yl)-ethyl]-1-phenoxy-3-aminopropan-2-ol by the reaction of 1-mesyloxy-2-(6,11-dihydrodibenz[b,e]oxepin-11-yl)-ethane (m.p. 64° – 66°C.) with 1-phenoxy-2-hydroxy-3-ethylamino-propane; yield 50% of theory; m.p. of the oxalate: 127° – 128°C.;

N-methyl-N-[3-(6,11-dihydrodibenz[b,e]oxepin-11-yl)-propyl]-1-phenoxy-3-aminopropan-2-ol by the reaction of 1-mesyloxy-3-(6,11-dihydrodibenz[b,e]-oxepin-11-yl)-propane (m.p. 88° – 90°C.) with 1-phenoxy-2-hydroxy-3-methylaminopropane; yield 53% of theory; m.p. of the oxalate: 100° – 103°C.;

N-methyl-N-[2-(6,11-dihydrodibenz[b,e]oxepin-11-yl)-propyl]-1-phenoxy-3-aminopropan-2-ol by the reaction of N-methyl-N-2-(6,11-dihydrodibenz[b,e]oxepin-11-yl)-propyl-1-amine (b.p. 158° – 160°C./0.05 mm.Hg.; from N-formyl-N-2-(6,11-dihydrodibenz[b,e]oxepin-11-yl)-propyl-1-amine (oil)) with phenyl glycidyl ether; yield 41.5% of theory; m.p. of the oxalate: 136° – 138°C.;

N-methyl-N-[2-(6,11-dihydrodibenz[b,e]oxepin-11-yl)-ethyl]-1-cyclohexyloxy-3-aminopropan-2-ol by the reaction of N-methyl-N-2-(6,11-dihydrodibenz[b,e]oxepin-11-yl)-ethylamine (b.p. 154° – 161°C./0.1 mm.Hg.) with 1-cyclohexyl glycidyl ether; yield 64.5% of theory; the compound was isolated as its amorphous oxalate; and N-methyl-N-[2-(5H-dibenzo[a,d]cyclohepten-5-yl)-ethyl]-1-phenoxy-3-aminopropan-2-ol by the reaction of N-methyl-N-2-(5H-dibenzo[a,d]cyclohepten-5-yl)ethylamine (b.p. 145° – 150°C./0.01 mm.Hg.; from N-formyl-N-2-(5H-dibenzo[a,d]cyclohepten-5-yl)-ethylamine (oil)) with phenyl glycidyl ether; yield 74.5% of theory; m.p. of the oxalate: 134° – 135°C.

The pharmacological effectiveness of the compounds in accordance with the invention and namely their effectiveness as cardiac and circulatory agents was evaluated by the increase in the heart minute volume. A criterion of the improvement of the blood supply to the organs lies in the increase of the heart minute volume as measured in the aorta of unanesthetized dogs following oral application of an appropriate pharmaceutical.

The tests were carried out on unanesthetized dogs having electromagnetic flowmeters chronically implanted in the aorta ascendens. The mechanical zero line was determined by means of simultaneously chronically implanted sealing flaps or by means of the exact adjustment of an electronic gate of the electro flowmeter. The test compounds were administered to the animal through stomach tubes. All of the compounds were employed dissolved in 10 ml distilled water to which 5% "Lutrol 9" (polyethylene oxide molecular weight - 400) had been added.

The following compounds were employed in the test procedure:

A — N-Methyl-N-[2-(6,11-dihydrodibenz[b,e]oxepin-11-yl-ethyl]-1-amino-3-phenoxy-propan-2-ol B — N-Methyl-N-[3-(6,11-dihydrodibenz[b,e]oxepin-11-yl)-propyl]-1-phenoxy-3-aminopropan-2-ol C — N-Ethyl-N-[2-(6,11-dihydrodibenz[b,e]oxepin-11-yl)-ethyl]-1-phenoxy-3-aminopropan-2-ol D — N-Methyl-N-[2-(10,11-dihydro-5H-dibenzo[a,d]cyclohepten-5-yl)-ethyl]-1-phenoxy-3-aminopropan-2-ol E — N-Ethyl-N-[1,1-dimethyl-2-(10,11-dihydro-5H-dibenzo[a,d]-cyclohepten-5-yl)-ethyl]-1-phenoxy-3-aminopropan-2-ol F — N-Methyl-N-[3-(10,11-dihydro-5H-dibenzo[a,d]cyclohepten-5-yl)-propyl]-1-phenoxy-3-aminopropan-2-ol G — N-Methyl-N-[2-(6,11dihydrodibenz[b,e]oxepin-11-yl)-propyl]-1-phenoxy-3-aminopropan-2-ol H — N-Methyl-N-[2-(6,11-dihydrodibenz[b,e]oxepin-11-yl)-ethyl]-1-cyclohexyloxy-3-aminopropan-2-ol I — N-Methyl-N-[2-(5H-dibenzo[a,d]cyclohepten-5-yl)-ethyl]-1-phenoxy-3-aminopropan-2-ol J — N-Methyl-N-[2-thiaxanthen-9-yl)-ethyl]-1-phenoxy-3-aminopropan-2-ol K* — COMPLAMIN xantinolnicotinate = 7-[2-Hydroxy-3-(N-methyl-$\beta$-hydroxyethylamino)-propyl]-theophylline L* — N-Methyl-N-[2-(6,11-dihydrodibenz[b,e]oxepin-11-yl)-ethyl]-1-(3-methyl-phenoxy)-2-hydroxy-3-amino-propane.

*Included for comparison purposes.

The compounds in accordance with the invention exhibit, i.e., are possessed of, special cardiac and circulatory activities and specifically of circulation stimulating activities. In the test procedures, the known compound (COMPLAMIN), xantinolnicotinate = 7-[2-hydroxy-3-(N-methyl-$\beta$-hydroxyethylamino)-propyl]-theophylline (Compound K), and N-methyl-N-2-(6,11-dihydrodibenz[b,e]oxepin-11-yl)-ethyl]-1-(3-methyl-phenoxy)-2-hydroxy-3-aminopropane (Compound L) were employed as comparison compounds.

The results were as follows:

TABLE

INCREASE IN THE BLOOD TIME VOLUME IN THE AORTA OF UNANESTHETIZED DOGS

| COMPOUND | DOSES MG/KG ORAL | MAX. INCREASE OF BLOOD TIME VOLUME IN % AS COMPARED TO THE CONTROL (=100%) |
|---|---|---|
| K | 25.0 | 110 |
| L | 0.5 | 115 |
| A | 0.5 | 149 |
| B | 0.5 | 140 |
| C | 0.5 | 167 |
| D | 0.5 | 125 |
| E | 0.5 | 137 |
| F | 0.5 | 135 |
| G | 0.5 | 128 |
| H | 0.5 | 123 |
| I | 0.5 | 120 |
| J | 0.5 | 133 |

Results

It can be seen from the preceding Table that 25.0 mg/kg xantinolnicotinate (oral) produced an increase in the heart minute volume of from 100 to 110%. The result was reproducible in each instance so that it can be taken as the comparison value. The novel compounds of the invention were administered in a dosage of 0.5 mg/kg, that is 1/50 of the dose of xantinolnicotinate. This consequently establishes for the compounds of the invention a marked superiority with respect to effect produced i.e., increase in heart minute volume in relation to xantinolnicotinate and this was true for every compound tested. Furthermore, it is evident that all compounds of the invention are more effective than the compound N-methyl-N-[2-(6,11-dihydrodibenz[b,e]oxapin-11-yl)-ethyl]-1-(3-methyl-phenoxy)-2-hydroxy-3-aminopropane.

Thus, it can be seen that the compounds of the invention administered in low dosages (0.5 mg/kg, oral) produce in the unanesthetized dog an increase in the peripheral blood circulation of the organs by an emptying of of venous blood storage depots, i.e, through an increase in the heart minute volume.

As indicated hereinbefore, the compounds of the present invention are useful for the treatment of conditions associated with cardiac and impaired circulatory phenomena and for this purpose the active compounds are associated with a pharmaceutically acceptable carrier in a form suitable for administration both perorally or parenterally.

The dosage of the novel compounds of the present invention for the treatment of the conditions as set out above, depends on the age, weight and condition of the patient being treated. Generally speaking, for adult oral administration, the preferred unit dosage is 1 mg – 50 mg of active compound with a suitable pharmaceutical diluent and/or lubricant.

The new compounds (I) according to the present invention and salts thereof can be administered enterally and parenterally in liquid or solid form. Thus, the present invention provides pharmaceutical compositions comprising at least one of the new compounds of the present invention, in admixture with a solid or liquid pharmaceutical diluent or carrier. As injection medium, it is preferred to use water which contains the usual additives for injection solutions, for example stabilizing agents, solubilizing agents and buffers. Additives of this kind include, for example, tartrate and citrate buffers, ethanol, complex-forming agents (for example ethylenediamine-tetraacetic acid and the nontoxic salts thereof) and high molecular weight polymers (for example liquid polyethylene oxide) for viscosity regulation. Solid carrier materials include, for example, starch, lactose, mannitol, methyl cellulose, talc, highly dispersed silicic acids, high molecular weight fatty acids (for example stearic acid), gelatine, agar-agar, calcium phosphate, magnesium stearate, animal and vegetable fats and solid high molecular weight polymers (for example polyethylene glycols). Compositions which are suitable for oral administration can, if desired, contain flavoring and/or sweetening materials.

It will be understood that athe the and examples are illustrative but not limitative of the present invention and that other embodiments within the spirit and scope of the invention will suggest themselves to those skilled in the art.

What is claimed is:

1. Tricyclic substituted aminoalcohol compound of the formula

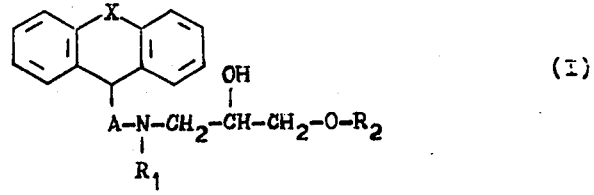

wherein
X is ethylene, vinylene, oxygen, sulfur, or oxamethylene,
A is straight-chained or branched alkylene of from 2 to 5 carbon atoms,
$R_1$ is alkyl of up to 3 carbon atoms; and
$R_2$ is cyclohexyl or phenyl;
and the physiologically compatible salts thereof.

2. Aminoalcohol compound as claimed in claim 1 wherein X is ethylene.

3. Aminoalcohol compound as claimed in claim 1 wherein X is vinylene.

4. Aminoalcohol compound as claimed in claim 1 wherein X is oxygen.

5. Aminoalcohol compound as claimed in claim 1 wherein X is sulfur.

6. Aminoalcohol compound as claimed in claim 1 wherein X is oxamethylene.

7. Aminoalcohol compound as claimed in claim 1 wherein $R_2$ is cyclohexyl.

8. Aminoalcohol compound as claimed in claim 1 wherein $R_2$ is phenyl.

9. Aminoalcohol compound as claimed in claim 1 designated N-methyl-N-[2-(6,11-dihydrodibenz[b,e]oxepin-11-yl-ethyl]-1-amino-3-phenoxy-propan-2-ol.

10. Aminoalcohol compound as claimed in claim 1 designated N-ethyl-N-[1,1-dimethyl-2-(10,11-dihydro-5H-dibenzo[a,d]cyclohepten-5-yl)-ethyl]-1-phenoxy-3-aminopropan-2-ol.

11. Aminoalcohol compound as claimed in claim 1 designated N-methyl-N-[3-(10,11-dihydro-5H-dibenzo[a,d]cyclohepten-5-yl)propyl]-1-phenoxy-3-aminopropan-2-ol.

12. Aminoalcohol compound as claimed in claim 1 designated N-ethyl-N-[2-(6,11-dihydrodibenz[b,e]oxepin-11-yl)-ethyl]-1-phenoxy-3-aminopropan-2-ol.

13. Aminoalcohol compound as claimed in claim 1 designated N-methyl-N-[3-(6,11-dihydrodibenz[b,e]oxepin-11-yl)propyl]-1-phenoxy-3-aminopropan-2-ol.

* * * * *